United States Patent [19]

Cabanes et al.

[11] Patent Number: 5,116,878
[45] Date of Patent: May 26, 1992

[54] MEDICINAL COMPOSITION FOR THE TREATMENT AND PREVENTION OF THE SYMPTOMS OF HEART FAILURE, CONTAINING A VASOCONSTRICTOR ALPHA-STIMULANT AGENT AS ACTIVE PRINCIPLE

[75] Inventors: Laure Cabanes; Alain Lockhart; Simon Weber, all of Paris, France

[73] Assignee: Universite de Paris V, Paris, France

[21] Appl. No.: 366,183

[22] Filed: Jun. 14, 1989

[30] Foreign Application Priority Data

May 16, 1989 [FR] France .................. 89 06380

[51] Int. Cl.⁵ .................................. A61K 31/135
[52] U.S. Cl. ............................. 514/653; 514/930
[58] Field of Search ..................... 514/653, 930

[56] References Cited

U.S. PATENT DOCUMENTS

| | | | |
|---|---|---|---|
| 2,359,707 | 10/1944 | Baltzly et al. | 564/343 |
| 3,787,571 | 1/1974 | Higuchi | 514/653 |
| 3,891,757 | 6/1975 | Higuchi | 514/653 |
| 3,968,245 | 7/1976 | Higuchi | 514/653 |
| 4,080,471 | 3/1978 | Carlsson et al. | 514/653 |
| 4,083,992 | 4/1978 | Smith | 514/653 |
| 4,853,216 | 8/1989 | Koslo et al. | 514/930 |

OTHER PUBLICATIONS

Pharmaceutical Dispensing, Third Edition (1947) Husa pp. 312–319; Husa Brothers, Iowa City, Iowa.
The Handbook of Nonprescription Drugs, 8th edition, American Pharmaceutical Association, Publisher, copyright 1986 pp. 172–173.
L. Cabanes et al., "Bronchial Hyperresponsiveness to Methacholine in Patients with Impaired Left Ventricular Function", published May 18, 1989 *The New England Journal of Medicine*, 320(20), pp. 1317–1322.

Primary Examiner—Frederick E. Waddell
Assistant Examiner—Raymond J. Henley, III
Attorney, Agent, or Firm—Sandler, Greenblum, & Bernstein

[57] ABSTRACT

This medicinal composition for the treatment and prevention of the symptoms of heart failure contains, by way of active principle, at least one compound chosen from 2-amino-1-(2,5-dimethoxyphenyl)-1-propanol (methoxamine) and its pharmaceutically acceptable salts, and it is presented in a form which can be administered by inhalation (aerosol or nebulizate).

It was demonstrated, in particular, that the administration of methoxamine-HCl by inhalation, at a unit dosage of 10 mg. in the form of a 2% (w/v) solution in physiological saline, decreases airways resistance in subjects suffering from decompensated left ventricular failure, and increases the exertion tolerance of patients suffering from compensated left vetricular failure, whether the latter is of ischemic origin or otherwise.

9 Claims, 1 Drawing Sheet

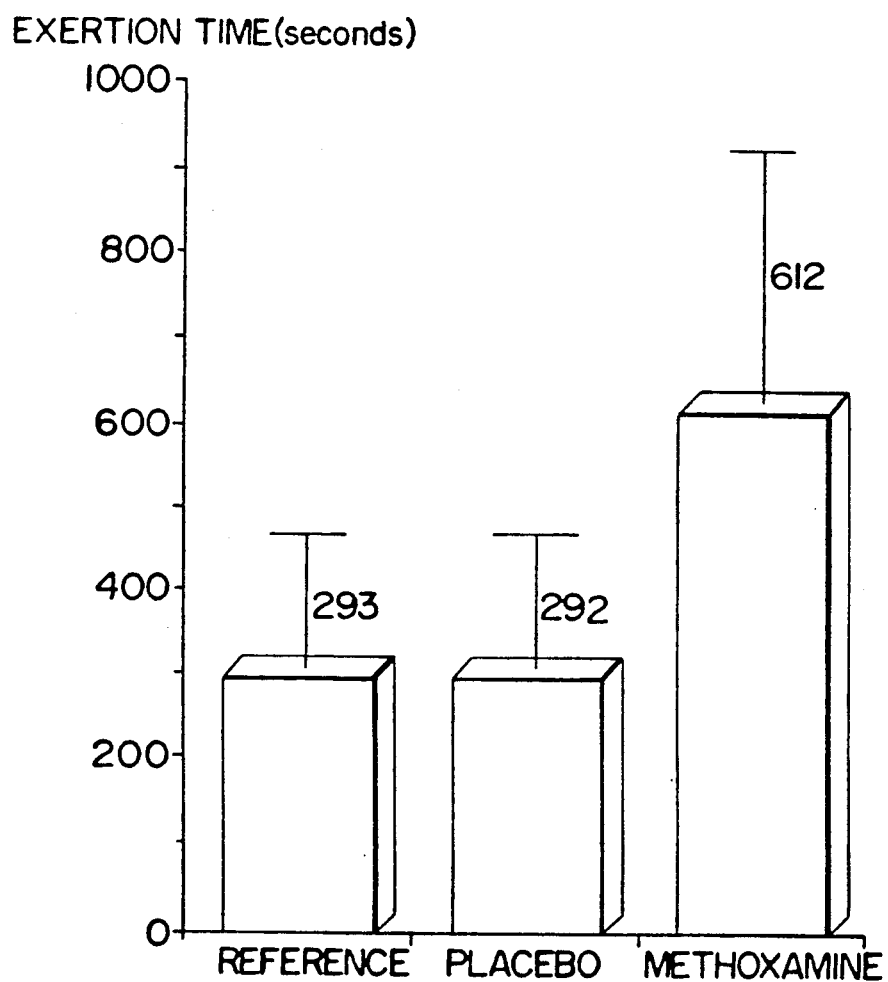

MEDICINAL COMPOSITION FOR THE TREATMENT AND PREVENTION OF THE SYMPTOMS OF HEART FAILURE, CONTAINING A VASOCONSTRICTOR ALPHA-STIMULANT AGENT AS ACTIVE PRINCIPLE

FIELD OF THE INVENTION

The present invention relates to a novel therapeutic application of a compound belonging to the category of vasoconstrictor alpha-stimulants, and of its pharmaceutically acceptable salts, this compound being 2-amino-1-(2,5-dimethoxyphenyl)-1-propanol, represented by the formula:

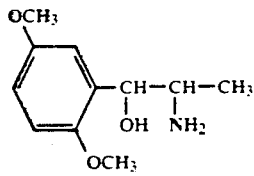

and known by the International Nonproprietory Name of methoxamine. For this novel therapeutic indication according to the invention, which is that of the treatment and prevention of the symptoms of heart failure, methoxamine and its salts are presented in a novel pharmaceutical dosage form and applied according to a novel administration route.

BACKGROUND OF THE ART

On the basis of the observation of symptoms of bronchial obstruction in patients suffering from heart failure, the present inventors first showed that the administration of the cholinergic agonist methacholine to patients suffering from left ventricular failure caused a bronchial obstruction at doses identical to those which were active in asthmatic subjects, this effect not being observed in patients exhibiting coronary insufficiency but normal left ventricular function. In view of the fact that the vessels which irrigate the bronchi drain into the left heart, the present inventors administered methoxamine-HCl, a potent vasoconstrictor, as a pretreatment via the respiratory tract (inhalation), and they demonstrated that this administration of methoxamine enables the bronchoconstriction induced by the inhalation of methacholine to be prevented in these patients suffering from left ventricular failure. The inventors then demonstrated that the administration of methoxamine by inhalation was capable:

- of decreasing the resistance of the airways in subjects suffering from decompensated left ventricular (pulmonary edema and subedema); and
- of increasing the exertion tolerance of patients suffering from compensated left ventricular failure, whether the latter is of ischemic origin or otherwise.

DETAILED DESCRIPTION OF THE INVENTION

The subject of the present invention is hence, in the first place, a medicinal composition for the treatment and prevention of the symptoms of heart failure, which contains, by way of active principle, at least one compound chosen from 2-amino-1-(2,5-dimethoxyphenyl)-1-propanol and its pharmaceutically acceptable salts, and which is presented in a form which can be administered by inhalation.

The therapeutic application of the present invention hence relates to methoxamine and its pharmaceutically acceptable salts with acids and quaternary ammonium derivatives. As addition salts with acids, there may be mentioned the salts formed with inorganic acids such as hydrochloric acid, hydrobromic acid, sulfuric acid, nitric acid or phosphoric acid; as well as the salts formed with organic acids such as acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and hydroxybenzenesulfonic acids. Methoxamine hydrochloride may be mentioned more especially.

The medicinal composition according to the invention is presented, in particular, in the form of an aerosol or a nebulisate, the non-propellent portion of the composition consisting of the active principle in physiological solution buffered to neutral pH or a pH close to neutrality. The concentration of active principle in this solution is between approximately 0.1% and approximately 10% (w/v). In particular, a concentration falling within the range of approximately 2-5% (w/v) may be used.

The propellent agent is a pharmaceutically acceptable gas chosen, in particular, from inert gases such as nitrogen, air, oxygen, halogenated aliphatic hydrocarbons such as dichlorodifluoromethane, and mixtures thereof.

The relative proportions of the nonpropellent to the propellent portion are the proportions commonly used by the specialist in pharmaceutical formulation for the preparation of nebulisates and aerosols intended for the administration of medicinal principles.

The medicinal product according to the invention is intended for the treatment and prevention, in man and animals, of symptoms of left ventricular failure, irrespective of its etiology, both in a compensated phase and in a phase of decompensation. The various indications which may be mentioned are the treatment and prevention of exertion dyspnea, of resting dyspnea, of paroxysmal nocturnal dyspnea and of pulmonary edema and subedema.

It has also been possible to establish the mechanism of this therapeutic effect:

In left ventricular failure, compensated or decompensated, as a result of the rise in hydrostatic pressure in the left cavities, a rise takes place in the pressure in the bronchial circulation which is responsible for a thickening and edema of the bronchial submucosa, which is in turn responsible for a bronchial obstruction contributing to the dyspnea of heart failure patients. Methoxamine, an alpha-stimulant, as a result of its potent bronchoconstrictor effect, forestalls and corrects this vasodilation of the bronchial circulation giving rise to the bronchial obstruction. In order that this effect may be beneficial from a therapeutic standpoint, it is essential to administer the vasoconstrictor alpha-stimulant agent topically (in this instance, by inhalation through the nose or mouth) in order to obtain only a local effect of vasoconstriction of the bronchial circulation without a systemic effect (generalized vasoconstriction), the hemodynamic consequences of which would be deleterious in the heart failure patient.

The medicinal product according to the invention may be prescribed as a continuous treatment, or alternatively as an occasional treatment, for example, before intense exertion on the part of the heart failure patient, thereby permitting presentation in pressurized containers of the "aerosol can" type or in nebulizers. As regards the dosage of the medicinal product according to the invention, it may be pointed out that the doses to be administered vary according to the duration of the treatment, the frequency of administration, the patient and the nature and severity of the disease. A unit dose ranging from approximately 0.1 to approximately 100 mg, for example a unit dose of approximately 10 mg, may be mentioned. The daily dosage can be, by way of example, from 1 to 10 inhalations per day, equivalent to 1 to 1000 mg per day.

The subject of the present invention is also the use of 2-amino-1-(2,5-dimethoxyphenyl)-1-propanol and its pharmaceutically acceptable salts for manufacturing a medicinal composition presented in a form which can be administered by inhalation, for the treatment and prevention of the symptoms of heart failure.

Finally, the subject of the invention is a method for preparing a medicinal composition intended for the treatment and prevention of the symptoms of heart failure, wherein at least one compound chosen from 2-amino-(2,5-dimethoxyphenyl)-1-propanol and its pharmaceutically acceptable salts is dissolved in a physiological solution, and wherein the solution thereby obtained is put into a form which can be administered by inhalation.

Demonstration of the action of methoxamine-HCl, administered by inhalation, on the dyspnea of heart failure patients.

1—Selection of patients

Ten adult patients suffering from severe secondary left ventricular failure, due either to coronary insufficiency or to a dilated cardiomyopathy, underwent this study. All the patients were in NYHA (New York Heart Association) functional category III for dyspnea at the time of the study, which was conducted between September 1988 and March 1989. All the patients exhibited a left ventricular ejection fraction, measured by isotopic biplane angiography (using technetium-99$^m$), of less than 35 percent.

Moreover, these patients all had a reproducible exertion tolerance threshold, defined as follows:

The patients were subjected twice, at an interval of 24 hours, to the same exertion test of walking on a moving belt, limited by dyspnea; the exertion in this test is of the constant-load type, with a constant speed of travel of the moving belt and a constant slope, known as a rectangular type exercise. The length of time the patient walks before becoming out-of-breath is measured. Patients were selected whose exertion tolerance threshold varied by less than 30 seconds over these two tests.

2—Protocol procedure

Days 1 and 2:

The patients were subjected again to the two exertion tests in order to check the reproducibility of the exertion tolerance. The exertion times thereby obtained represented the reference values.

Days 3 and 4:

The patients were each subjected to the same two exertion tests at an interval of 24 hours, 15 minutes after receiving either placebo (physiological saline alone) or 10 mg of methoxamine-HCl (in the preparation described below), by a method of administration also described below. This part of the study was conducted according to a crossover, randomized and double-blind model.

3—Preparation of methoxamine-HCl

A 2% solution of methoxamine-HCl in physiological saline buffered to pH 7 (solution containing 20 mg per milliliter) was prepared. This solution was packaged in a Devilbiss 646 nebulizer (Somerset, Pa.), the propellant used being pure oxygen.

4—Method of administration

The administrations were performed by the same doctor between 3 p.m. and 6 p.m. at the same time of day for a given patient. The blood pressure and cardiac output were followed throughout the trials using an automated oscillometric method (Dinamap TN Critikon).

The methoxamine-HCl preparation and the physiological saline were administered with the abovementioned nebulizer, which was activated during the inspiration phase of respiration by means of a French-Rosenthal dosimeter (Laboratory for Applied Immunology, Baltimore) under a pressure of pure oxygen of 138 kPa. The nebulisation time was adjusted to approximately one second, and the number of breaths selected was that needed for obtaining the nebulisation of a quantity of 10 mg of methoxamine-HCl (equivalent to ½ ml of solution).

5—Results

The mean exercise time in the first two tests ($D_1$-$D_2$) was 293 seconds; the mean exercise time after placebo was 292 seconds, and after methoxamine-HCl, 612 seconds. Inhaled methoxamine-HCl hence leads to a significant increase, at least to the 1/100 level ($p<0.01$), or even to the 1/1000 level, relative to the placebo, in the exertion time. These results are plotted on the diagram constituting figure 1/1 of the attached drawing.

At the same time, no adverse effect was observed, and good tolerance of the medicinal product was noted, both from the standpoint of the bronchial mucosa and from a general standpoint.

| FORMULATION EXAMPLE: 20-ml aerosol generator | | |
|---|---|---|
| (A) | Methoxamine-HCl | 100 mg |
|  | Physiological saline buffered to pH 7 qs | 5 ml |
| (B) | Nitrogen | 15 ml |

What is claimed is:

1. A method of treating the symptoms of left ventricular dysfunction, the method which comprises:
   (a) providing a medicinal composition comprising as its active principle a therapeutically effective amount of at least one compound selected from the group consisting of 2-amino-1-(2,5-dimethoxyphenyl) -1-propanol and pharmaceutically acceptable salts thereof, and which medicinal composition is in a form which can be administered by inhalation; and
   (b) administering said medicinal composition by inhalation to a patient in order to treat symptoms of left ventricular dysfunction in said patient.

2. The method as claimed in claim 1, wherein said providing step (a) comprises:
   (a) dissolving said active principle in a physiological solution; and (b) placing said solution in a form which can be administered by inhalation.

3. The method as claimed in claim 2, wherein said physiological solution has a concentration of about 0.1 to 10% (w/v) of active principle.

4. The method as claimed in claim 3, wherein said physiological solution has a concentration of from about 2 to 5% (w/v) of active principle.

5. The method as claimed in claim 1, wherein said medicinal composition is administered on the basis of 1 to 1000 mg per day.

6. A method of preventing the symptoms of left ventricular dysfunction, the method which comprises:
  (a) providing a medicinal composition comprising as its active principle a therapeutically effective amount of at least one compound selected from the group consisting of 2-amino-1-(2,5-dimethoxyphenyl)-1-propanol and pharmaceutically acceptable salts thereof, and which medicinal composition is in a form which can be administered by inhalation; and
  (b) administering said medicinal composition by inhalation prior to the onset of left ventricular dysfunction symptoms in a patient, in order to prevent the onset of said left ventricular dysfunction symptoms.

7. The method as claimed in claim 6, wherein said providing step (a) comprises:
  (a) dissolving said active principle in a physiological solution; and
  (b) placing said solution in a form which can be administered by inhalation.

8. The method as claimed in claim 7, wherein said physiological solution has a concentration of from about 0.1 to 10% (w/v) of active principle.

9. The method as claimed in claim 8, wherein said physiological solution has a concentration of form about 2 to 5% (w/v) of active principle.

* * * * *

UNITED STATES PATENT AND TRADEMARK OFFICE
CERTIFICATE OF CORRECTION

PATENT NO. : 5,116,878
DATED : May 26, 1992
INVENTOR(S) : L. CABANES et al.

It is certified that error appears in the above-indentified patent and that said Letters Patent is hereby corrected as shown below:

On cover page, item [54], TITLE, line 1, change "MEDICIAL" to ---MEDICINAL---.

Item [57], "ABSTRACT", line 8, change "nebulizate" to ---nebulisate---.

Item [57], "ABSTRACT", line 15, change "vetricular" to ---ventricular---.

At column 1, line 54 insert ---failure--- after "ventricular".

At column 3, line 27 change "2-amino-(2,5-dimethoxyphenyl)-1-propanol" to ---2-amino-1-(2,5-dimethoxyphenyl)-1-propanol---.

At column 6, line 18 (claim 9, line 2) change "form" to ---from---.

Signed and Sealed this

Thirtieth Day of January, 1996

Attest:

BRUCE LEHMAN

Attesting Officer     Commissioner of Patents and Trademarks